(12) United States Patent
Sutherland

(10) Patent No.: US 11,318,029 B2
(45) Date of Patent: May 3, 2022

(54) PULMONARY ARTERIAL COMPLIANCE ENHANCEMENT DEVICE

(71) Applicant: Michael Warren Sutherland, Groton, MA (US)

(72) Inventor: Michael Warren Sutherland, Groton, MA (US)

(*) Notice: Subject to any disclaimer, the term of this patent is extended or adjusted under 35 U.S.C. 154(b) by 94 days.

(21) Appl. No.: 16/438,443

(22) Filed: Jun. 11, 2019

(65) Prior Publication Data

US 2019/0380850 A1 Dec. 19, 2019

Related U.S. Application Data

(60) Provisional application No. 62/684,708, filed on Jun. 13, 2018.

(51) Int. Cl.
*A61F 2/844* (2013.01)
*A61F 2/848* (2013.01)
*A61F 2/86* (2013.01)
*A61F 2/966* (2013.01)
*A61F 2/82* (2013.01)

(52) U.S. Cl.
CPC .............. *A61F 2/844* (2013.01); *A61F 2/848* (2013.01); *A61F 2/86* (2013.01); *A61F 2/966* (2013.01); *A61F 2002/825* (2013.01); *A61F 2002/8483* (2013.01); *A61F 2210/0014* (2013.01); *A61F 2220/0041* (2013.01); *A61F 2230/006* (2013.01); *A61F 2250/001* (2013.01); *A61F 2250/0006* (2013.01)

(58) Field of Classification Search
CPC .. A61F 2/844; A61F 2/848; A61F 2/86; A61F 2/2427; A61F 2/243; A61F 2/2439; A61F 2002/825; A61F 2002/8483; A61F 2220/0041; A61F 2250/001; A61F 2250/0006; A61F 2/2442; A61F 2/2451
See application file for complete search history.

(56) References Cited

U.S. PATENT DOCUMENTS

| | | | |
|---|---|---|---|
| 6,951,571 B1* | 10/2005 | Srivastava | A61F 2/2418 623/1.24 |
| 9,039,725 B1 | 5/2015 | Vollmers et al. | |
| 9,610,391 B2 | 4/2017 | Vollmers et al. | |
| 9,987,153 B2 | 6/2018 | Scandurra et al. | |
| 10,350,397 B2 | 7/2019 | Scandurra et al. | |
| 2016/0235526 A1* | 8/2016 | Lashinski | A61F 2/2409 |
| 2017/0086974 A1* | 3/2017 | Lashinski | A61F 2/2427 |
| 2017/0209253 A1* | 7/2017 | Lashinski | A61F 2/2412 |
| 2017/0246436 A1* | 8/2017 | Bak-Boychuk | A61B 17/00234 |

FOREIGN PATENT DOCUMENTS

WO WO2018075552 A1 4/2018

* cited by examiner

*Primary Examiner* — Kathleen S Holwerda
*Assistant Examiner* — Uyen N Vo
(74) *Attorney, Agent, or Firm* — Helen S Liu; Liu Law Office

(57) ABSTRACT

Devices and methods for treating heart disease by increasing the pulmonary vascular compliance and thereby decreasing the right ventricular afterload are disclosed. Devices may include a means for reducing the cross-sectional area of the pulmonary artery during diastole and allowing the cross-sectional area to increase during systole.

11 Claims, 9 Drawing Sheets

PULMONARY ARTERIAL COMPLIANCE ENHANCEMENT DEVICE

CROSS-REFERENCE TO RELATED APPLICATION

This application claims priority to and the benefit of U.S. Provisional Application No. 62/684,708, entitled "Pulmonary arterial Compliance Enhancement Device," filed on Jun. 13, 2018, which is incorporated herein in its entirety by reference.

FIELD

The present teachings relate to methods and devices for pulmonary hypertension and heart failure. In particular, the present teachings relate to methods and devices for treating pulmonary hypertension by increasing the pulmonary arterial compliance and thereby reducing the right ventricle after-load.

BACKGROUND

Heart failure is a condition effecting millions of people worldwide. Right-sided and left-sided heart failure can both lead to pulmonary hypertension which can in-turn lead to right heart failure. There exists a need for devices and methods for treating pulmonary arterial hypertension and right heart failure. Pulmonary arterial hypertension is described by the increased pulmonary vascular resistance and decreased pulmonary arterial compliance. While methods of treating increased pulmonary vascular resistance may include pharmacological treatments or diuretics, there exists a need for treating decreased pulmonary arterial compliance. To that end, devices and methods are disclosed that increase the volumetric pulmonary arterial compliance in order to reduce the right ventricular after-load and to treat heart failure.

SUMMARY

In general, the present teachings concerns treating right heart failure and pulmonary hypertension. To this end, devices and methods are disclosed herein which may include implanting a compliant element to the pulmonary arterial trunk and left and right pulmonary arteries to increase the volumetric compliance of the pulmonary arterial vasculature. Furthermore, devices and methods are disclosed herein for treating pulmonary hypertension which may include accessing the pulmonary artery trunk, delivery an implant and adjusting the implant as needed to increase the compliance of the pulmonary artery and reduce the after-load on the right ventricle. Additionally, devices and methods are disclosed which may include implanting a device inside a patient's pulmonary artery in order to increase the volumetric compliance of the pulmonary artery and providing a means for adjusting the amount of volumetric compliance of the artery and further providing a means for repositioning, retrieving, or removing the implant as needed to treat a patient.

In some embodiments, an implantable compliant device is provided. The device includes elongate elements that push outward on the pulmonary artery walls thereby effectively ovalizing the hydraulic cross section of the pulmonary artery. The device is configured to ovalize the pulmonary artery trunk during diastole and is further configured to compress and allow the pulmonary artery to resume a circular cross section during systole. The inventive device may feature anchoring elements to anchor the implant to the pulmonary artery. The inventive device may be configured such that the outward force on the pulmonary artery wall is adjustable during implant delivery. The inventive device may be configured such that the ovalization of the pulmonary artery trunk results in a pre-determined cross-sectional area change in the pulmonary artery. The inventive device may be configured such that the cross-sectional area change and the compliance of the device are both separately adjustable. In some embodiments, the elongate outward pushing elements are specially configured semi-rigid or flexible wire forms. The wire forms of the inventive device may be made from any suitable material and may include braided wire rope, stainless steel wire, wound wire coils, laser-cut hypodermic tubing, nitinol wire or tubing, or polymeric tubing.

In some embodiments, a stent-like implantable compliant device is provided. The stent like device is anchored to the pulmonary artery on the distal end and on the proximal end and is configured to generate significant torque on the pulmonary artery. The torsional force generated by the compliant device may be sufficient to reduce the internal diameter of the pulmonary artery trunk, left pulmonary artery, and/or right pulmonary artery. The device may be further configured to unwind or relax in response to changes in hydraulic pressure inside the pulmonary artery. The torsional action of the device may be configured to allow the internal diameter of the pulmonary artery to expand temporarily during systole and then return to its reduced volume in diastole.

In some embodiments, a stent-like implantable compliant device is provided. The stent-like implant may include a large proximal end and may be bifurcated into two distal segments. The large proximal end may be anchored to the pulmonary artery trunk and the two distal segments may be anchored to the left and right pulmonary arteries respectively. The inventive device may be constrained during delivery with significant torsional mechanical stress stored in the distal segments. The device may then be implanted into the pulmonary vasculature and then allowed to resume a more relaxed configuration, thereby imparting significant torque to the left and right pulmonary arteries simultaneously. This torsion may be configured to reduce the hydraulic area of the pulmonary arteries. The torsional stiffness of the implant may be further configured such that during systole the hydraulic area of the pulmonary arteries is increased and in diastole the area of the pulmonary arteries is reduced.

DETAILED DESCRIPTION

Figure 1:
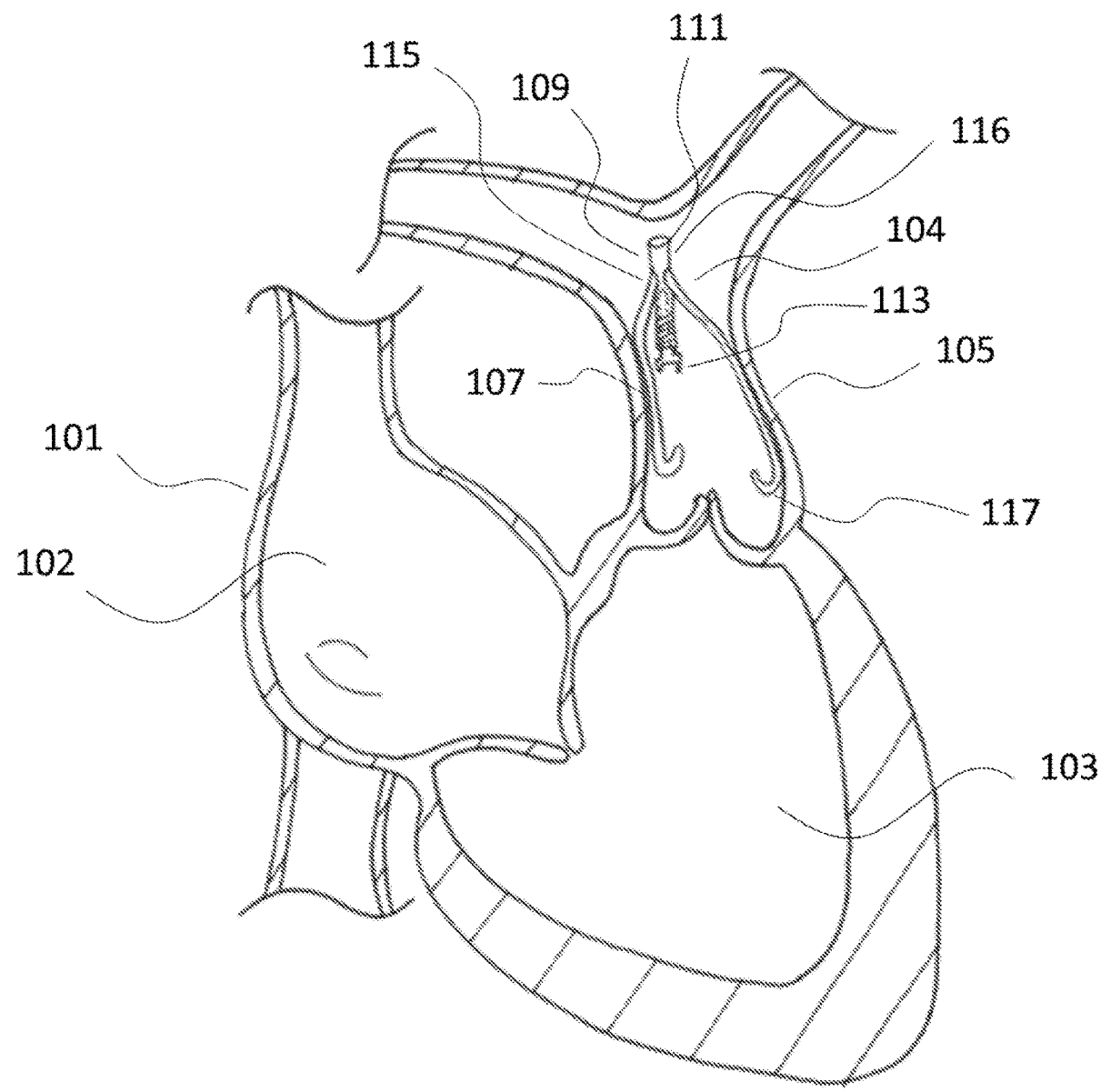
FIG. 1 depicts an exemplary device implanted in the pulmonary artery trunk of a heart according to some embodiments of the present teachings.

Certain specific details are set forth in the following description and Figures to provide an understanding of various embodiments of the present teachings. Those of ordinary skill in the relevant art will understand that they can practice other embodiments of the present teachings without one or more of the details described herein. Thus, it is not the intention of the Applicants to restrict or in any way limit the scope of the appended claims to such details. While various processes are described with reference to steps and sequences in the following disclosure, the steps and sequences of steps should not be taken as required to practice all embodiments of the present teachings. Thus, it is not the intention of the present teachings to restrict or in any way limit the scope of the appended claims to such steps or sequences of steps.

Unless otherwise defined, explicitly or implicitly by usage herein, all technical and scientific terms used herein have the same meaning as those which are commonly understood by one of ordinary skill in the art to which this present teachings pertain. Methods and materials similar or equivalent to those described herein may be used in the practice or testing of the present teachings. In case of conflict between a common meaning and a definition presented in this document, latter definition will control. The materials, methods, and examples presented herein are illustrative only and not intended to be limiting.

Unless expressly stated otherwise, the term "embodiment" as used herein refers to an embodiment of the present teachings.

Unless a different point of reference is clear from the context in which they are used, the point of reference for the terms "proximal" and "distal" is to be understood as being the position of a practitioner who would be implanting, is implanting, or had implanted a device into a patient's atrial septum from the right atrium side of a patient's heart. An example of a context when a different point of reference is implied is when the description involves radial distances away from the longitudinal axis or center of a device, in which case the point of reference is the longitudinal axis or center so that "proximal" refers to locations which are nearer to the longitudinal axis or center and "distal" to locations which are more distant from the longitudinal axis or center. Another example of a context when a different point of reference is implied is when the description involves distance towards a clinician. Under that circumstance, the term "proximal" means close to the clinician (less into the body) and "distal" shall mean away from the clinician (further into the body). In positioning a medical device from a downstream access point, "distal" is more upstream and "proximal" is more downstream.

As used herein, the terms "subject" and "patient" refer to an animal, such as a mammal, including livestock, pets, and preferably a human. Specific examples of "subjects" and "patients" include, but are not limited to, individuals requiring medical assistance and, in particular, requiring treatment for symptoms of a heart failure.

As used herein, the term "lumen" means a canal, duct, generally tubular space or cavity in the body of a subject, including veins, arteries, blood vessels, capillaries, intestines, and the like. The term "lumen" can also refer to a tubular space in a catheter, a sheath, or the like in a device.

As used herein, the term "catheter" or "sheath" encompasses any conduit, including any hollow instrument, that can be inserted into a patient's body to treat diseases, to administer or withdraw fluids, or to perform a surgical procedure. The catheters of the present teachings can be placed within the vascular, urological, gastrointestinal, ophthalmic, and other bodily system, and may be inserted into any suitable bodily lumen, cavity, or duct. For example, a catheter or a sheath of the present teachings can be used to penetrate a body tissue or interstitial cavities and/or provide a conduit for injecting a solution or gas. The term "catheter" or "sheath" is also intended to encompass any elongate body capable of serving as a conduit for one or more of the ablation, expandable, or sensing elements. In the context of coaxial instruments, the term "catheter" or "sheath" can encompass either the outer catheter body or sheath or other instruments that can be introduced through such a sheath. The use of the term "catheter" should not be construed as meaning only a single instrument but rather is used to encompass both singular and plural instruments, including coaxial, nested, and other tandem arrangements. Moreover, the terms "sheath" or "catheter" are sometime used interchangeably to describe catheters having at least one lumen through which an instrument or treatment can pass.

Unless otherwise specified, all numbers expressing quantities, measurements, and other properties or parameters used in the specification and claims are to be understood as being modified in all instances by the term "about." Accordingly, unless otherwise indicated, it should be understood that the numerical parameters set forth in the following specification and attached claims are approximations. At the very least, and not as an attempt to limit the application of the doctrine of equivalents to the scope of the claims, numerical parameters should be read in light of the number of reported significant digits and the application of ordinary rounding techniques.

FIG. 1 depicts a cross-sectional view of a patient's heart 101 including a right atrium 102 and a right ventricle 103 and shows an exemplary compliant implant device 104 implanted in the pulmonary artery trunk 105. The implant device features two elongate compliant wire elements 107 that are shown pushing outward on the walls of the pulmonary artery. The two wires 107 are joined at the distal joint assembly 109 by any suitable means including crimping, welding, mechanical fit, or adhesive usage. The distal joint assembly includes a distal threaded tube 111 and a proximal adjustment screw 113. The threaded tube includes two side holes 115, 116 through which the wires are threaded. The proximal adjustment screw is configured to engage with threads on the inside of the threaded tube such that turning the screw element results in the screw moving either distally or proximally relative to the distal joint depending on the direction of rotation of the screw. The distal end of the screw may include a conical point or may include a specialized bearing surface treatment, shape, or texture. The wires may be configured with a relaxed configuration in which there is some pre-determined acute angle between the two wires. The proximal screw element is configured such that it pushes outwardly on the two wires when it is rotated into the threaded tube thereby increasing the angle between the two wires. The action of the wire and proximal screw is configured such that this motion of the wires is reversible by unscrewing the proximal screw. In this manner, the proximal screw element and distal joint assembly represents a means for adjusting the amount of ovalization of the pulmonary artery and thereby adjusting the potential amount of volumetric compliance of the pulmonary artery.

The exemplary compliant wires of FIG. 1 may be made from any suitable material including stainless steel, nitinol, titanium, PEEK, polyurethane, platinum, platinum iridium, silver, gold, or other metallic or polymeric materials. The complaint wires may be made from super elastic or shape memory materials. The compliant wires may be formed from braided or twisted strands or as a cable. The wires may be made from electrical discharge machined or laser cut hollow tubing. The compliant wires may include atraumatic tip features 117. The atraumatic tip features may include widened ends, polymeric end caps, pigtailed end features, or flexible articulating end segments. Polymeric end caps may be attached to the ends of the compliant wires by heat shrinking, over-molding, gluing, press-fit, or other suitable means.

Figure 2:
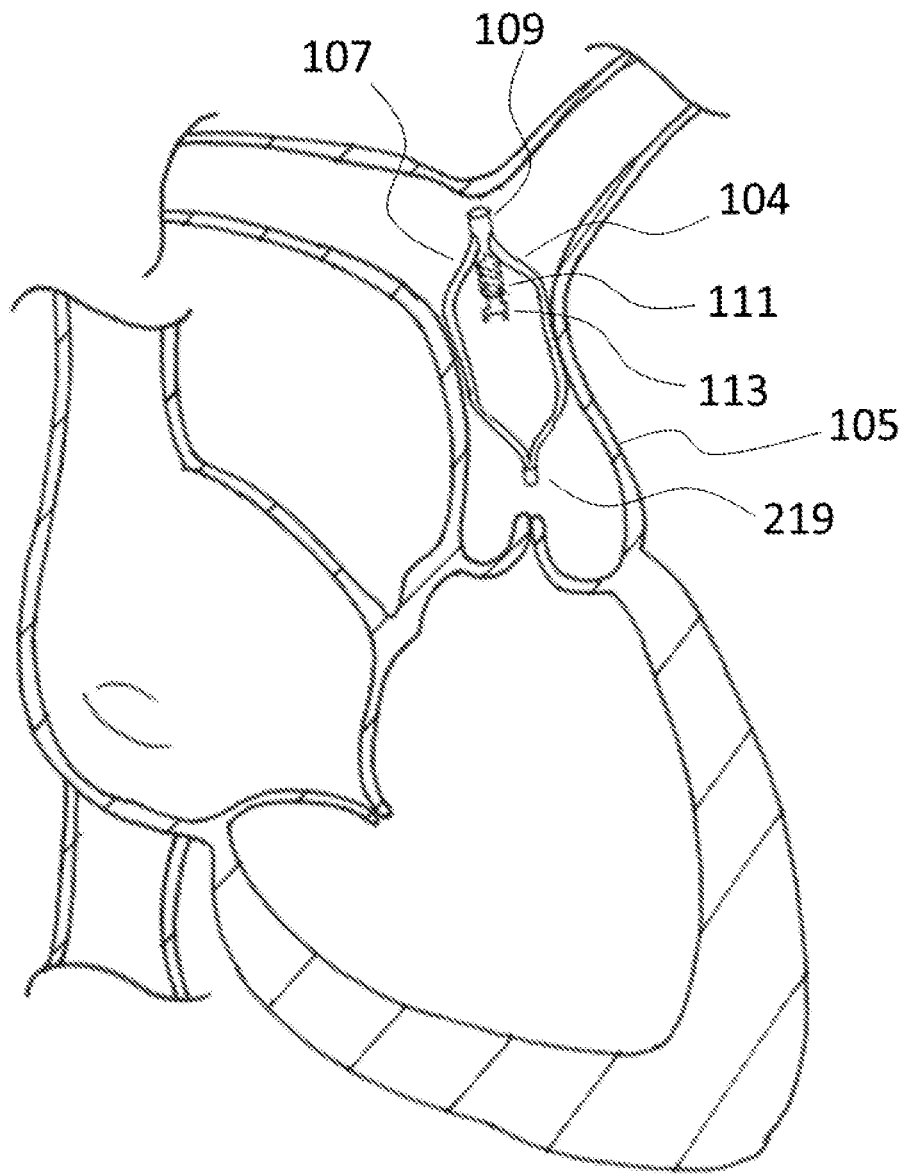
FIG. 2 illustrates an exemplary device implanted in the pulmonary artery trunk of a heart according to some embodiments of the present teachings.

Referring now to FIG. 2, some embodiments of the present teachings are depicted. An exemplary compliant device 104 is again depicted in a patient's pulmonary artery trunk 105. The compliant device features two compliant elongate wires 107 joined at a distal joint assembly 109. The joint assembly includes a distal threaded tube 111 and a proximal adjustment screw 113. The proximal adjustment screw is configured to engage the threaded tube and to reversibly push on the elongate wires in order to apply outward force on the pulmonary artery trunk. The complaint wires are attached at the proximal joint 119. The proximal joint may be formed by any suitable means including, for example, crimping, welding, twisting, knotting, or threading a nut over the wires.

Figure 3:
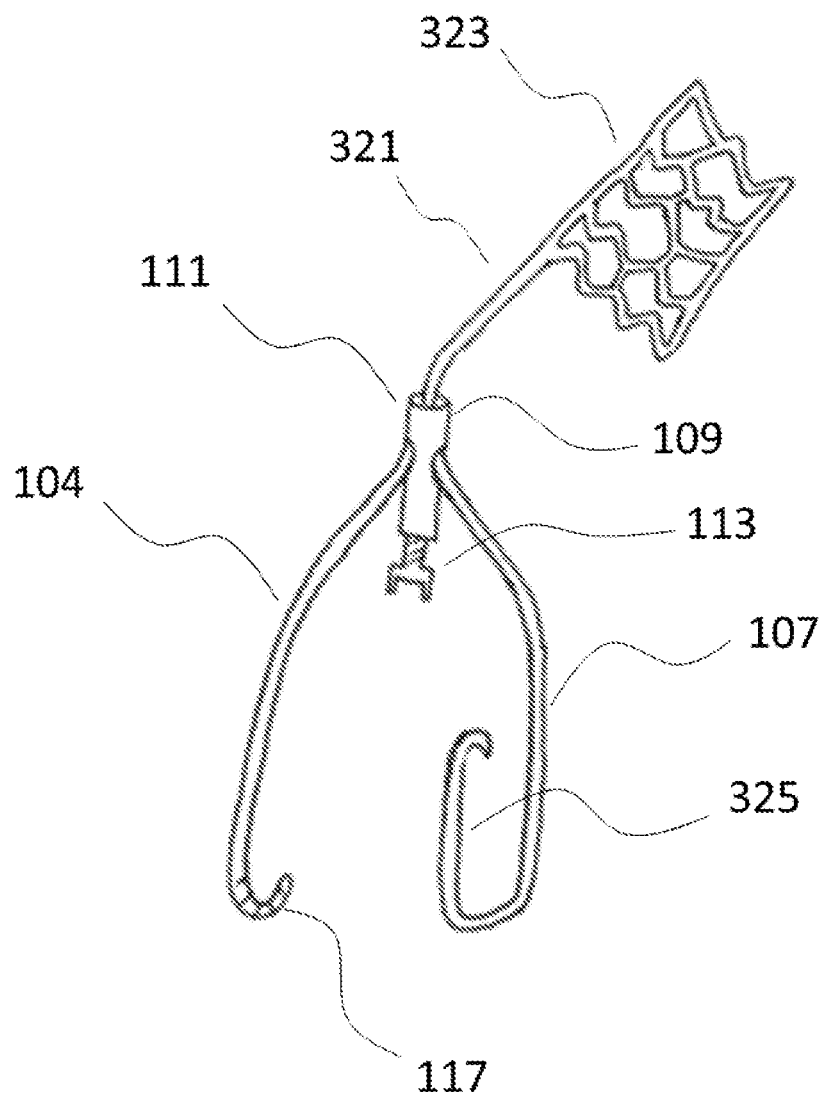
FIG. 3 illustrates an exemplary device according to some embodiments of the present teachings.

Turning now to FIG. 3, some embodiments of the present teachings are depicted. An exemplary compliant device 104 is depicted. The complaint device features two complaint wires 107 joined at the distal joint assembly 109. The joint assembly includes a distal threaded tube 111 and a proximal adjustment screw 113. The proximal adjustment screw may be configured in the same manner as depicted in FIGS. 1 and 2 and may be used to supply an adjustable amount of outward force on the complaint wires. The distal joint assembly is connected to a distal anchoring arm 321 which is connected to a distal anchor 323. The distal anchoring arm may be connected to the distal joint assembly by any suitable means, including by crimping, swaging, gluing or use of adhesives, welding, soldering, screwing, or a mechanical fit. The distal anchoring arm may instead be an extension of the distal joint assembly such that the anchoring arm and joint assembly represent a single component of the inventive device. The distal anchoring arm may be made of any suitable material, including those materials listed above as potential materials of manufacture for the compliant wires. The distal anchoring arm may be made of a laser cut hypotube or may be made of super-elastic nitinol. The distal anchor may be composed of a tubular stent-like structure. The distal anchor is configured to expand into the distal aspect of a pulmonary artery in order to anchor the implantable device to the body. The distal anchor may be specifically configured for implantation into the left or right branch of the pulmonary artery. The distal anchor may be connected to the anchoring arm by any suitable means, such as crimping, swaging, threading, welding, or soldering. In some embodiments, the distal anchoring arm and the distal anchor are formed from a continuous section of laser cut stainless steel or nitinol hypodermic tubing. The distal anchor may be made of any suitable material including stainless steel, polymeric materials, PET, nitinol, cobalt-chromium alloys, gold, titanium, or other metallic alloys. The distal anchor may be self-expanding or may be expanded by a balloon, or otherwise mechanically expanded.

The exemplary compliant wires of FIG. 3 include a hooked wire 325. The hooked wire is configured with a roughly 180-degree bend. The bend in the hooked wire is configured to engage the pulmonary artery along two points of contact in order to bring the total contact points of the compliant wires to three. The hooked wire is configured to further stabilize the implant in the pulmonary artery and to help prevent migration of the device and torsional movement of the device. The proximal most ends of the compliant wires features atraumatic tips 117 which may be simply curved inwards into the lumen of the pulmonary artery. The atraumatic tips may be made of a substantially more flexible or softer material than the body of the compliant wires.

Figure 4:
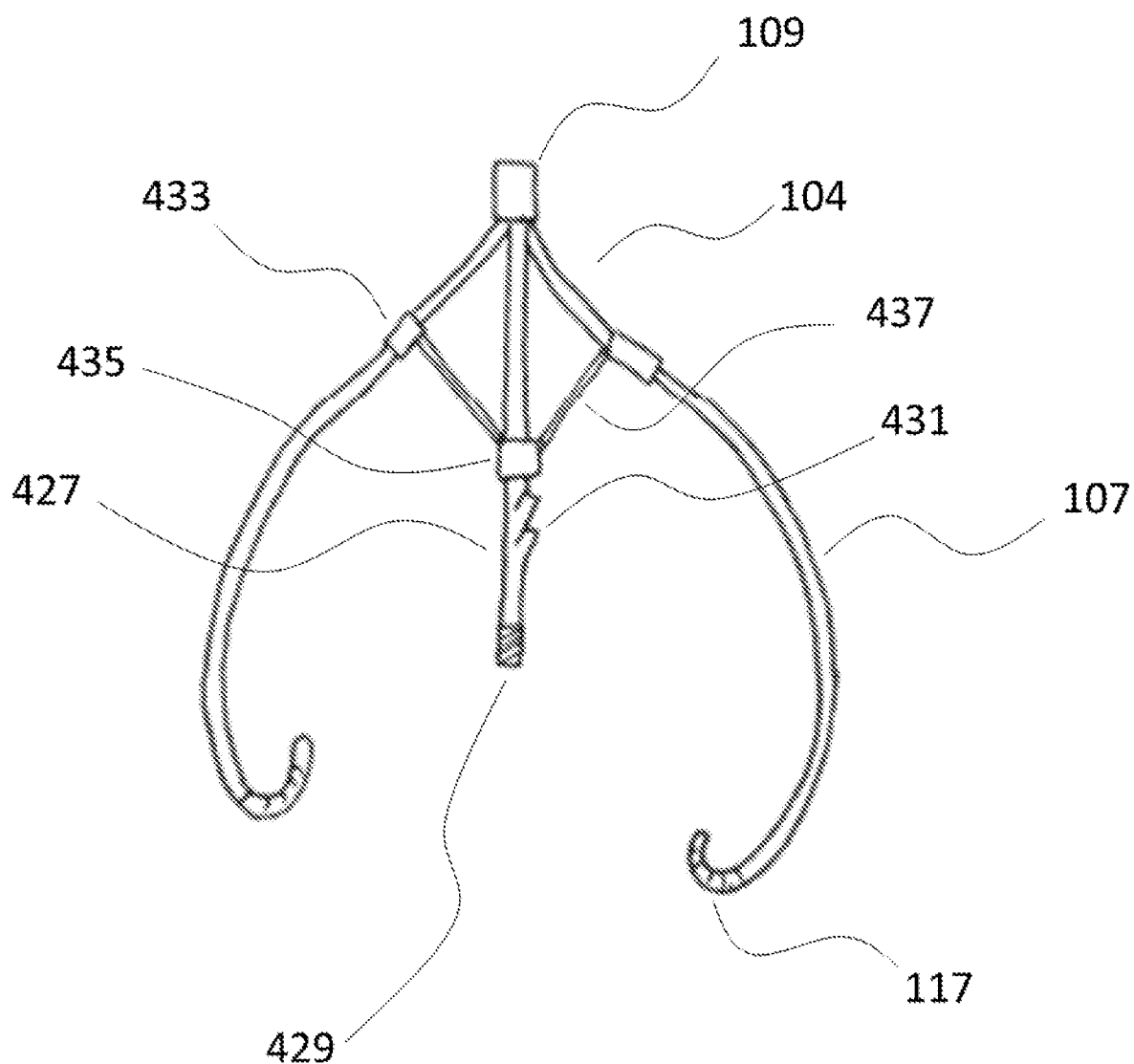
FIG. 4 illustrates an exemplary device according to some embodiments of the present teachings.

Turning now to FIG. 4, some embodiments of the present teachings are depicted. An exemplary compliant device 104 is depicted. The complaint device includes two compliant wires 107 connected at distal joint assembly 109. A central post 429 is also connected to the compliant wires at the distal joint assembly. The central post includes a proximal threaded end 429 which is configured to interface with a threaded delivery catheter. A sliding wire opening hinge element 435 slide-ably resides on the central post and connects to the complaint wires by way of struts 437. The distal ends of the struts are fixedly attached to the compliant wires by attachment features 433. The central post further includes flexible ratchet tines 431. The complaint wires of FIG. 4 include proximal atraumatic tip features 117.

The exemplary compliant device of FIG. 4 is configured to be delivered into the pulmonary artery of a patient in a collapsed state. The sliding hinge element 435 is configured to slide along the central post and features a coaxial connection to the central post. As the sliding hinge element coaxially slides distally along the post it passes by the ratchet tines which locks in the distal motion of the hinge element by preventing proximal migration of the hinge element. This distal sliding of the hinge element causes the struts to angle outward and in turn push outward on the compliant wires. The struts are configured to hinge relative to the sliding body of the hinge element and relative to the attachment features 433. These elements of FIG. 4 therefore represent a means of ovalizing a patient's pulmonary artery, controlling the amount of ovalization of the pulmonary artery, and thereby increasing the volumetric compliance of the pulmonary artery.

The distal joint assembly of FIG. 4 can be created by any of the means disclosed above including crimping, swaging, threading, gluing, soldering, welding or other means. For example, the distal joint assembly of FIG. 4 may be formed by providing an appropriately sized stainless steel tube which is configured to tightly contain the compliant wires and the central post and then mechanically swaging the tube to create an interference fit. The sliding hinge element can be manufactured by any reasonable means including laser cutting a stainless steel or Nitinol hypodermic tube. In some embodiments, the sliding hinge element and struts are formed from a single laser cut stainless steel tube. The attachment features may be attached to the struts and compliant wires by crimping, swaging, welding, gluing or other mechanical means. In some embodiments, the attachment features are simply crimped platinum-iridium marker bands.

In some embodiments, the sliding hinge element, struts, and attachment features may be manufactured as a single polymeric component. In some embodiments, the hinge element, struts, and attachment features are configured to be injection molded as a single component and are configured to be over-molded directly onto the compliant wires. The central post of FIG. 4 can be made from any suitable material including stainless steel, PEEK, other polymeric materials, Nitinol, or other metallic materials. The ratchet tines of can be attached to the central post by any of the means referenced above including welding, crimping, swaging, gluing, or over molding. The ratchet tines may be machined directly into the central post, for example, the central post may be made from a laser cut Nitinol tube and the tines may then be heat-formed into a barbed position as shown in FIG. 4.

The exemplary compliant wires of FIG. 4 may be manufactured as conventional wires or may instead be configured with a multifilament construction including braided cables, bundles of 3-7 wires, wound coils, or other constructions and configurations. The compliant wires of FIG. 4 may be manufactured by laser cutting a metallic tube. The compliant wires may instead be made of a polymeric material and may feature a rectangular cross-section, or may instead be a tape-like, I-beam, or other cross-sectional shape.

Still referring to FIG. 4, in some embodiments, the compliant device is configured to be delivered through a catheter. The catheter may include an outer shaft and an inner catheter. The outer shaft may be configured to push distally on the sliding hinge element thereby advancing the hinge element along the central post and thereby expanding the complaint wires and ovalizing the pulmonary artery. The inner catheter may be configured to be threaded onto the central post to substantially maintain the position of the compliant device relative to the pulmonary artery. The inner catheter may be configured to transmit torque in order to unthread the catheter from the implant once the desired amount of ovalization or force has been applied to the patient's vasculature. In some embodiments, the inner catheter is releasable connected to the central post by other means including using a pull wire, lynch pin, compression fit, or rivet-like mechanism.

Figure 5:
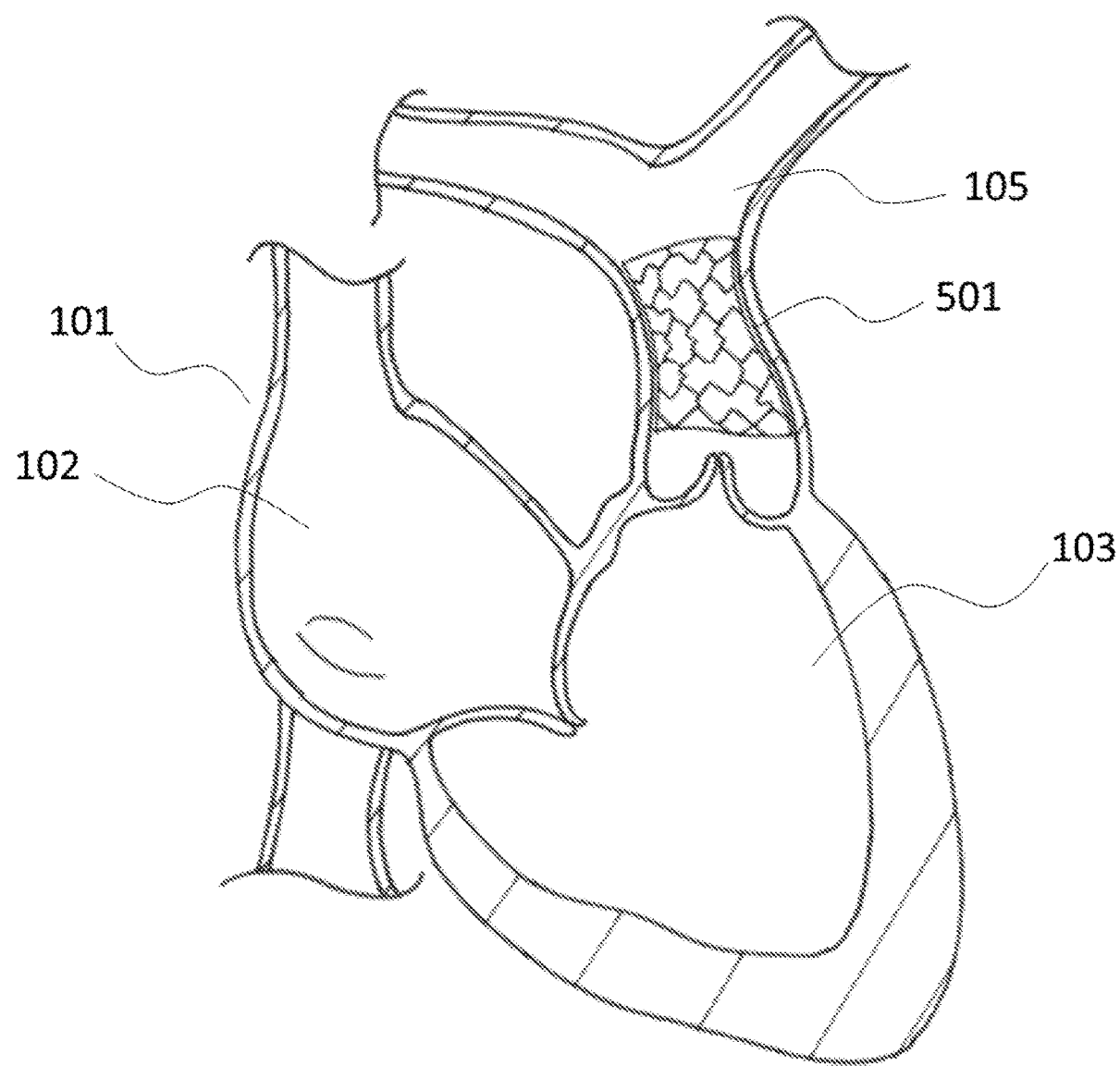
FIG. 5 illustrates an exemplary device implanted in the pulmonary artery trunk of a heart according to some embodiments of the present teachings.

Turning now to FIG. 5, some embodiments of the present teachings are depicted. FIG. 5 shows a cross-sectional view of a patient's heart 101 including a right atrium 102 and a right ventricle 103 and shows an exemplary stent-like compliant implant device 501 implanted in the pulmonary artery trunk 105. The stent-like compliant implant is configured to have a substantially oval cross section. The stent-like implant is configured such that under typical systolic arterial pressure the cross section of the implant deforms into a substantially circular cross section. The implant is further configured such that as the arterial pressure drops during diastole the implant resumes its more relaxed state with an ovalized cross section. In this manner the stent-like complaint implant of FIG. 5 represents a means of increasing the volumetric compliance of the pulmonary artery. In some embodiments, the stent-like implant may be configured to reside in the pulmonary artery trunk and one or both of the main branches of the pulmonary artery. In some embodiments, the implant may instead by made from multiple stent-like structures. For example, in some embodiments, a stent-like implant resides in the pulmonary artery trunk while a second and third stent-like implants reside in the left and right pulmonary artery branches. In some embodiments, the stent-like implant may be configured to be nested with other stent-like implants. For example, the first implant may be configured to apply a pre-determined amount of ovalizing stress to the pulmonary artery walls. Angiography or echocardiography may then be used to assess the amount of ovalization and the amount of additional pulmonary arterial compliance created by the implant. If desired, a second stent-like implant can be deployed inside the first stent-like implant to apply a second and larger pre-determined amount of ovalizing stress to the pulmonary artery walls. In some embodiments, multiple stent-like implants are designed to nest inside each other in order to adjust the amount of ovalization of the pulmonary artery and in order to fine-tune the resulting arterial pressure wave form.

The stent-like compliant implant of FIG. 5 may be made from any suitable material including stainless steel, Nitinol, titanium, cobalt-chromium alloy, tantalum alloy, or polymeric materials. The stent-like compliant implant can be configured to be delivered in a collapse configuration and then implanted in an expanded configuration. The expansion of the implant can be self-expanding, for example, like a self-expanding Nitinol stent, or may be balloon expanded or otherwise expanded by the delivery system. The stent-like compliant implant may be made by any suitable technology including laser-cutting, wire braiding, or stamping, rolling, and welding. In some embodiments, the stent-like compliant implant is manufactured of Nitinol by laser cutting a strut pattern into Nitinol hypodermic tubing. The implant can then be expanded and heat set into an ovalized shape.

Figure 6:
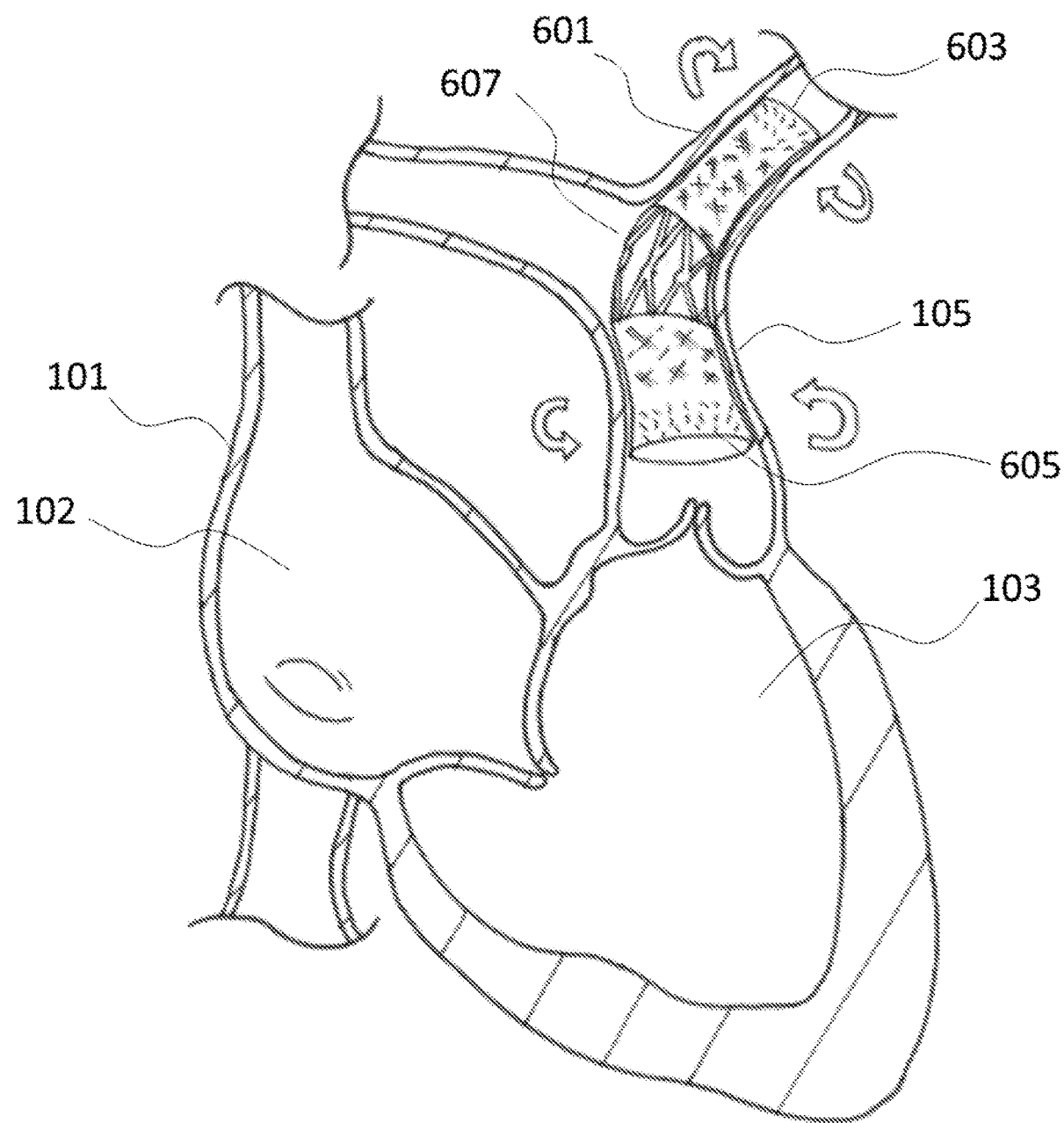
FIG. 6 illustrates an exemplary device implanted in the pulmonary artery trunk of a heart according to some embodiments of the present teachings.

Turning now to FIG. 6, some embodiments of the present teachings are depicted. FIG. 6 depicts a cross-sectional view of a patient's heart 101 including a right atrium 102 and a right ventricle 103 and shows an exemplary stent-like compliant implant device 601 implanted in the pulmonary artery trunk 105. The stent-like compliant device can be manufactured from any of the same materials and by any of the same methods as described above. The stent-like compliant device includes distal anchoring elements 603 and proximal anchoring elements 605. The distal and proximal anchoring elements are configured to secure the implant to the interior wall of the pulmonary artery trunk. The anchoring elements may be small barbs or hooks which engage the surface of the pulmonary artery. The anchoring elements may instead fasten the implant to the pulmonary artery by interference fit, for example, expanding the diameter of the anchoring section substantially beyond the normal internal diameter of the pulmonary artery trunk. In some embodiments, the anchoring elements include compliant materials such as expanded PTFE. In some embodiments, the anchoring elements include chemical fixation elements such as a material that becomes tacky when in contact with blood. In some embodiments, the anchoring elements include rotationally active elements, for example, the anchoring elements may include twisted finger-like protrusions which are designed to expand the outer diameter of the anchoring section on response to the torque applied by the pulmonary artery wall. The compliant device further includes a flow permitting waist section 607. The stent-like compliant device is configured to reside inside a patient's pulmonary artery trunk and either the left or right branch of the pulmonary artery. The stent-like compliant device is further configured to supply a significant amount of torsional force to the pulmonary artery. The torsional force is configured to partially collapse the internal diameter of the pulmonary artery trunk and thereby reduce the cross-sectional area of the pulmonary artery trunk. The torsional force is further configured such that this cross-sectional reduction is more significant during the low pressure diastolic phase of the heart cycle and is less significant during the high pressure systolic phase of the heart cycle. In this manner, the stent-like compliant device of FIG. 6 represents a means for adjusting the pressure wave of a patient's pulmonary artery by effectively increasing the pulmonary artery wall compliance.

In some embodiments of the present teachings, as shown in FIG. 6, the stent-like compliant device is delivered in a high-energy, wound-up state and the anchor elements are allowed to contact the walls of the pulmonary artery trunk in this state. The implant is then allowed to relax thereby imparting a twist on the pulmonary artery due to the torque stored in the device. In other embodiments, the stent-like compliant implant may be deployed in a relaxed state and then later torque may be applied to the implant through a delivery catheter. In some embodiments, a secondary torsional element can be added to the stent-like compliant device, for example, a trifilar torsional member may be advanced into the internal diameter of the implant and may be used to supply the torque to the implant. In some embodiments, the torque may be slowly applied to the tissue, for example, through a means such as biodegradeable elements which prevent the implant from imparting torque to the anatomy until after these elements degrade. In some embodiments, the amount of torque supplied by the implant may be adjusted, for example, through a ratcheting mechanism.

Figure 7:
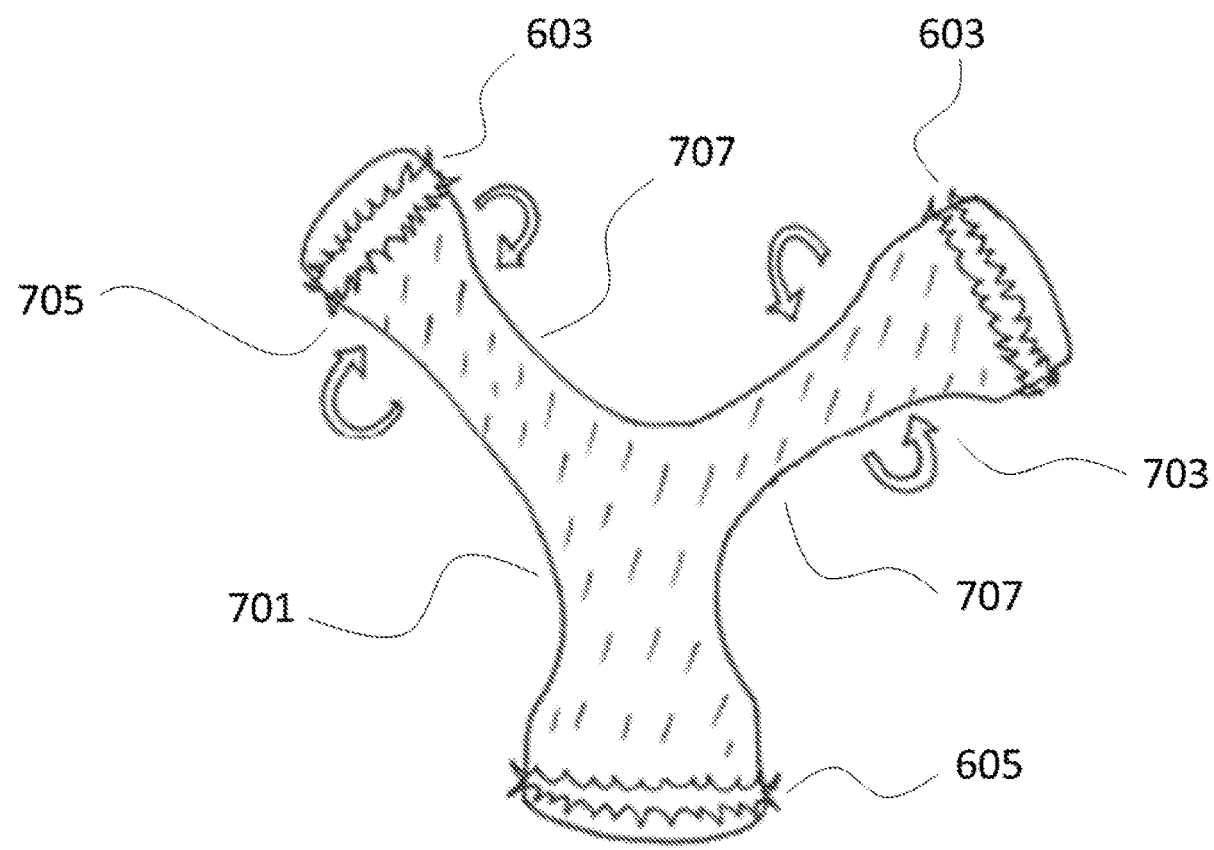
FIG. 7 illustrates an exemplary device according to some embodiments of the present teachings, where the exemplary device comprises a proximal anchoring element and a distal anchoring element.

Turning now to FIG. 7, some embodiments of the present teachings are depicted. FIG. 7 depicts a stent-like bifurcated compliant device 701 which includes proximal anchoring elements 605 and distal anchoring elements 603. The bifurcated compliant device includes a left arm 703 intended for implantation into the patients left pulmonary artery branch and a right arm 705 intended for implantation into the patient right pulmonary artery branch. The left and right arms of the compliant device may include narrowed waist sections 707. The stent-like compliant device may be partially or completely covered by a polymeric or biological material, such as ePTFE, PET, or mammalian pericardium. The stent-like compliant device may include expanded distal and proximal segments and narrowed central segments. The narrowed central segments may be configured to be substantially compliant while the expanded distal and proximal segments may be configured to be substantially rigid or non-compliant.

The compliant device including the left and right arms are configured such that they can be compressed into a delivery catheter. The left and right arms are further configured such that in a delivery configuration they are held under a significant amount of torsional stress. This stress can be maintained during delivery of the implant by any suitable means, for example, ridges on the internal diameter or external diameter of the implant may interface with the delivery system to maintain the torsional stress on the device during delivery. The left and right arms are further configured such that after delivering the implant to the pulmonary artery branches the implant is allowed to relax towards a lower stress state, thereby imparting significant torsion to the pulmonary artery branches and thereby reducing the effective cross-sectional area of the pulmonary artery trunk. The torsion supplied to the left and right arms and the amount of relaxation of the compliant device after implantation may be configured such that during the high pressure phase of the cardiac cycle the complaint device is under a first amount of torsional stress which increases the cross sectional blood flow area while during the low pressure phase of the cardiac cycle the compliant device is under a second and lower amount of torsional stress which reduces the cross sectional blood flow area.

Figure 8:
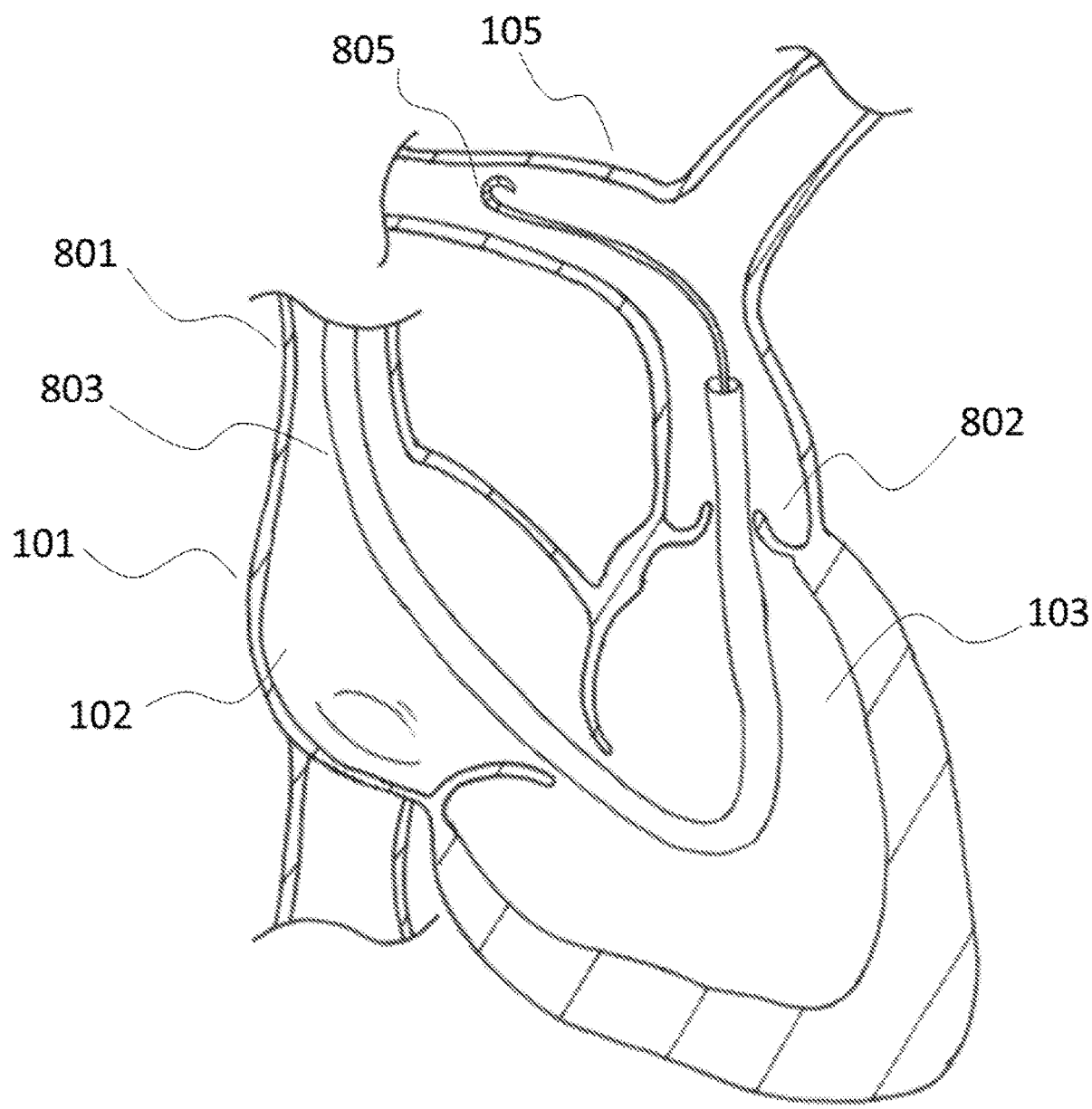
FIG. 8 illustrates an exemplary delivery system according to some embodiments of the present teachings.

Turning now to FIG. 8, a potential delivery system for the present teachings is depicted. FIG. 8 depicts a cross-sectional view of a patient's heart 101 including a right atrium 102, and right ventricle 103, and a pulmonary artery trunk 105. An exemplary delivery catheter 803 is depicted traversing through the patient's superior vena cava 801 into the right ventricle, across the patient's pulmonary valve 802 and into the pulmonary artery. The delivery system may be configured to be delivered over a standard interventional wire 805. The interventional wire could be any suitable wire, for example, a 0.035" "J" shaped wire may be used. The delivery catheter may be made from any suitable material including Nylon, polyether block amide (PEBAX), polyurethane, HDPE, FEP, and PTFE. The delivery catheter may be made from a laser cut stainless steel hypodermic tube. The delivery catheter may be made from a jacketed stainless steel or otherwise metallic coil. The delivery catheter may include braided support structure, for example braided stainless steel wires may run through the wall of the delivery catheter. The braided stainless wires may be round, rectangular, or square in cross-section and may be woven in any suitable braiding pattern. The delivery catheter may be pre-shaped for access to the pulmonary artery, for example, the catheter may be constructed from PEBAX heat flowed over a stainless steel braid pattern and then heat set into a shape designed to point towards the pulmonary artery. The delivery catheter may include steerable elements, such as pull wires positioned inside the wall of the catheter or inside the lumen of the catheter. The delivery catheter is sized appropriately for insertion into the vasculature. For example, the delivery catheter may feature a 4.3 mm outer diameter and a 3.3 mm inner diameter and may be suitable for insertion into a standard sized access sheath. In some embodiments, the delivery catheter is designed to enter into the body through the jugular vein and into the superior vena cava. In some embodiments, the delivery catheter is designed to enter into the body through the femoral vein and up through the inferior vena cava and into the right heart. Alternative forms of access to the right heart may be used, including radial arm access, central venous access, or minimally invasive access to the right heart and pulmonary artery.

Figure 9:
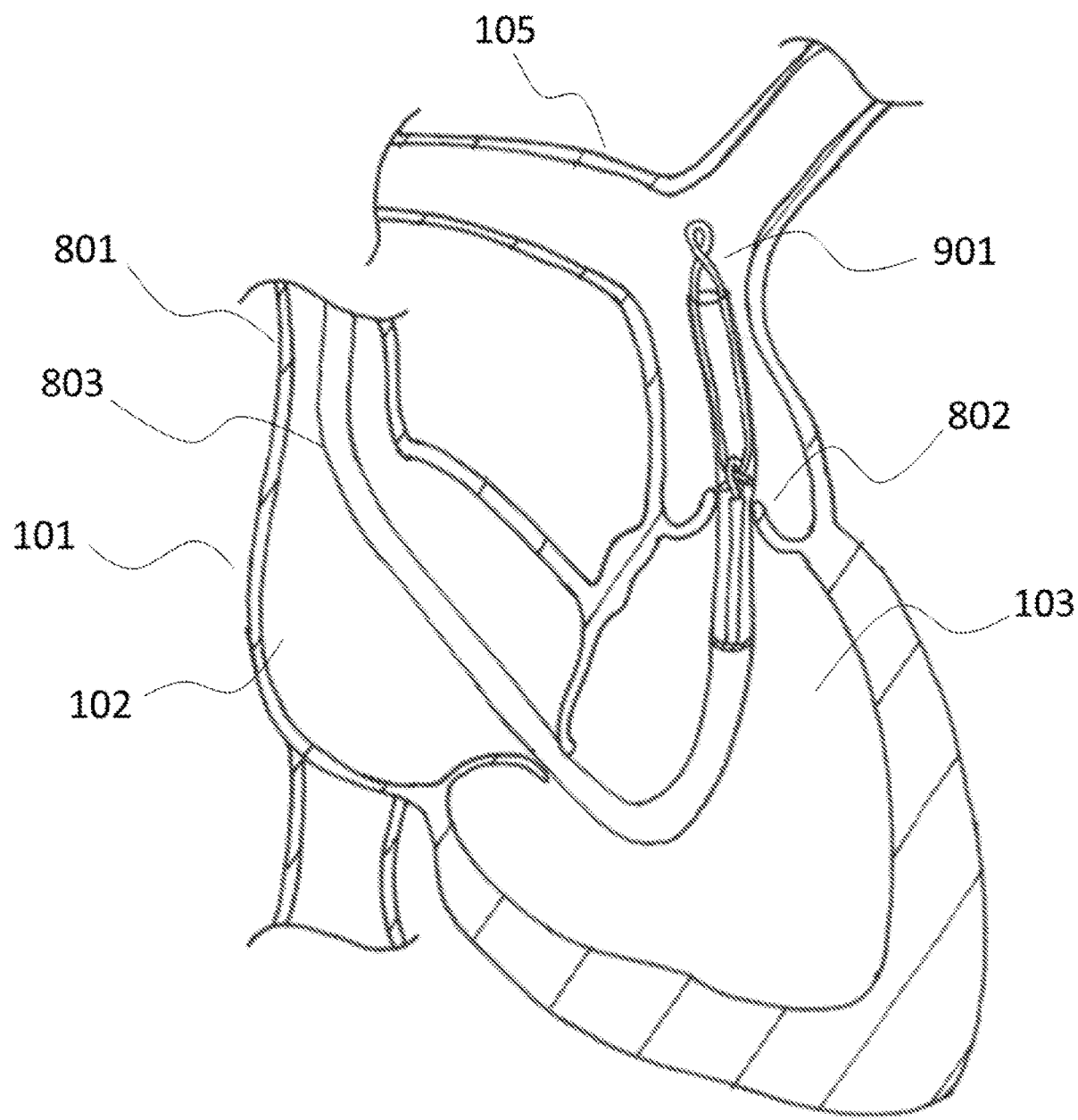
FIG. 9 illustrates an exemplary delivery system and an exemplary device where the exemplary device is releasably connected with the exemplary delivery system according to some embodiments of the present teachings.

Turning now to FIG. 9, some embodiments of the present teachings are depicted. In FIG. 9, a cross-sectional view of a patient's heart 101 including a right atrium 102, a right ventricle 103 and a pulmonary artery trunk 105 are depicted. A delivery catheter 803 is threaded through a superior vena cava 801 through the pulmonary valve 802 and into the pulmonary artery. Pre-loaded into the distal end of the delivery catheter is an exemplary implantable compliant device similar to those disclosed above. The exemplary compliant device is configured to be collapsed into a compressed configuration and loaded into the delivery catheter. The exemplary compliant implant device is further configured to be releasably constrained by the delivery catheter. The exemplary compliant device is configured to be pushed out into the patient's pulmonary artery trunk thereby engaging the target anatomy. The exemplary compliant implant device may than be adjusted as needed to increase the effective volumetric compliance of the pulmonary artery. The exemplary compliant device may be further configured to be recaptured and extracted if needed. The exemplary compliant device may be configured to be repositionable if needed. Once the desired treatment effect has been achieved the exemplary compliant device is configured to be released by the delivery system, and then the delivery system can be removed from the body, leaving behind the implantable compliant device.

Although the present teachings disclose the steps of delivery, deployment, and release of a cardiac implant, one skilled the in art would understand that these specific steps are treatment or implant specific and thus subject to change. Thus, specific embodiments disclosed in the present teachings should not be construed as limiting.

Various embodiments have been illustrated and described herein by way of examples, and one of ordinary skill in the art will appreciate that variations can be made without departing from the spirit and scope of the present teachings. The present teachings are capable of other embodiments or of being practiced or carried out in various other ways, for example, in combinations, all of which are within the scope of the present teachings and the appended claims, when applicable, explicitly or under the doctrine of equivalents. Also, it is to be understood that the phraseology and terminology employed herein is for the purpose of description and should not be construed as limiting.

I claim:

1. An implantable device for treating heart failure by increasing a patient's pulmonary artery compliance comprising:
   two compliant wires each having a proximal end and a distal end, wherein the two compliant wires form an angle in between;
   a distal joint assembly having a distal threaded tube and a proximal adjustment screw, wherein the proximal adjustment screw is configured to rotationally engage the distal threaded tube such that the proximal adjustment screw moves distally or proximally relative to the distal threaded tube;
   wherein the distal ends of the two compliant wires join the distal threaded tube through corresponding side holes on the distal threaded tube; and the proximal adjustment screw is configured to push onto the distal ends of the two compliant wires from inside the distal threaded tube and thereby adjusting the angle between the compliant wires; and
   wherein the proximal ends of the two compliant wires join together forming a proximal joint.

2. The device of claim 1, wherein the device has a first configuration where the two compliant wires form a first predetermined acute angle.

3. The device of claim 2, wherein the two compliant wires are configured to push outward on the walls of the pulmonary artery.

4. The device of claim 2, wherein the device has a second configuration where the two compliant wires form a second angle, and wherein the second angle is greater than the first predetermined acute angle.

5. The device of claim 4, wherein at the second configuration, the two compliant wires are configured to push the walls of the pulmonary artery further radially outward, and thereby change the amount of ovalization of the pulmonary artery.

6. The device of claim 1, wherein as the proximal adjustment screw moves distally relative to the distal threaded tube and pushes onto the distal ends of the compliant wires, the angle in between the two compliant wires increases.

7. The device of claim 1, wherein at least one of the two compliant wires has a 180-degree bend at its proximal end.

8. An implantable device for treating heart failure by increasing a patient's pulmonary artery compliance comprising:
   two compliant wires each having a proximal end and a distal end, wherein the two compliant wires form an angle in between;
   a distal joint assembly having a distal threaded tube and a proximal adjustment screw, wherein the proximal adjustment screw is configured to rotationally engage the distal threaded tube such that the proximal adjustment screw moves distally or proximally relative to the distal threaded tube;
   wherein the distal ends of the two compliant wires join the distal threaded tube through corresponding side holes on the distal threaded tube; and the proximal adjustment screw is configured to push onto the distal ends of the two compliant wires from inside the distal threaded tube and thereby adjusting the angle between the compliant wires; and
   a distal anchor joining the distal joint assembly by a distal anchoring arm.

9. The device of claim 8, wherein the distal anchor is configured to be positioned inside a left or a right branch of the pulmonary artery while the distal joint assembly of the device remains inside a pulmonary artery trunk.

10. The device of claim 8, wherein the distal anchor has a tubular stent structure.

11. An implantable device for treating heart failure by increasing a patient's pulmonary artery compliance comprising:
    two compliant wires each having a proximal end and a distal end, wherein the two compliant wires form an angle in between;
    a distal joint assembly having a distal threaded tube and a proximal adjustment screw, wherein the proximal adjustment screw is configured to rotationally engage the distal threaded tube such that the proximal adjustment screw moves distally or proximally relative to the distal threaded tube;
    wherein the distal ends of the two compliant wires join the distal threaded tube through corresponding side holes on the distal threaded tube; and the proximal adjustment screw is configured to push onto the distal ends of the plurality of compliant wires from inside the distal threaded tube and thereby adjusting the angle between the compliant wires; and
    wherein the proximal ends of the two compliant wires are adapted to curve inwards into the lumen of the pulmonary artery forming an atraumatic tip.

* * * * *